(12) United States Patent
Ochiai et al.

(10) Patent No.: US 8,192,761 B2
(45) Date of Patent: Jun. 5, 2012

(54) GRANULAR PREPARATION CONTAINING BIGUANIDE COMPOUND

(75) Inventors: Yasushi Ochiai, Ibaraki (JP); Yasuhiro Matsui, Ibaraki (JP)

(73) Assignee: Dainippon Sumitomo Pharma Co., Ltd., Osaka-shi, Osaka (JP)

( * ) Notice: Subject to any disclaimer, the term of this patent is extended or adjusted under 35 U.S.C. 154(b) by 171 days.

(21) Appl. No.: 11/912,463

(22) PCT Filed: Apr. 26, 2006

(86) PCT No.: PCT/JP2006/308711
§ 371 (c)(1),
(2), (4) Date: Oct. 24, 2007

(87) PCT Pub. No.: WO2006/118137
PCT Pub. Date: Nov. 9, 2006

(65) Prior Publication Data
US 2009/0130215 A1 May 21, 2009

(30) Foreign Application Priority Data
Apr. 26, 2005 (JP) .................... 2005-127360

(51) Int. Cl.
*A61K 9/14* (2006.01)
(52) U.S. Cl. ........................ 424/489; 514/866
(58) Field of Classification Search .......... None
See application file for complete search history.

(56) References Cited

U.S. PATENT DOCUMENTS

| 5,026,560 | A | * | 6/1991 | Makino et al. | 424/494 |
|---|---|---|---|---|---|
| 5,618,799 | A | | 4/1997 | Inagi et al. | |
| 5,955,106 | A | | 9/1999 | Moeckel et al. | |
| 6,413,541 | B1 | * | 7/2002 | Shirai et al. | 424/435 |
| 6,517,870 | B1 | * | 2/2003 | Nishii et al. | 424/489 |
| 6,559,187 | B2 | | 5/2003 | Chandran et al. | |
| 2003/0039699 | A1 | | 2/2003 | Ochiai et al. | |
| 2004/0202718 | A1 | | 10/2004 | Tyebji et al. | |
| 2005/0287207 | A1 | | 12/2005 | Koike et al. | |
| 2007/0053939 | A1 | | 3/2007 | Yokoyama et al. | |
| 2007/0218129 | A1 | | 9/2007 | Besse | |

FOREIGN PATENT DOCUMENTS

| DE | 4432757 | A1 | | 3/1996 |
|---|---|---|---|---|
| FR | 2858556 | A1 | | 2/2005 |
| JP | 08-012582 | A | | 1/1996 |
| JP | 2002-241267 | A | | 8/2002 |
| JP | 2002-332226 | A | | 11/2002 |
| JP | 2003-514012 | A | | 4/2003 |
| JP | 2004-149521 | A | | 5/2004 |
| JP | 2005-068116 | A | | 3/2005 |
| JP | 2005-139173 | A | | 6/2005 |
| WO | WO 99/55320 | A1 | | 11/1999 |
| WO | WO 01/35941 | A2 | | 5/2001 |
| WO | WO 03/099214 | A2 | | 12/2003 |
| WO | WO 2004110422 | A1 | * | 12/2004 |
| WO | WO 2005/072717 | A1 | | 8/2005 |

OTHER PUBLICATIONS

J Klancke. "Dissolution Testing of Orally Disintegrating Tablets." Dissolution Technologies, May 2003, pp. 6-8.*
Mesh to Micron Conversion Chart. http://www.colonialvirginiahpr.org/Experimental/meshmicron.htm, May 31, 2004 (as of internet archive), 3 pages.*
Kibbe et al., "Handbook of Pharmaceutical Excipients, 3rd Ed." (American Pharmaceutical Association, Jan. 1, 2001), pp. 143-145.
Oku et al., Nutrition Research, 16(4): 577-589 (1996).
European Patent Office, Extended European Search Report in EP 06 745 689 (Nov. 21, 2008).
European Patent Office, Extended European Search Report in EP 10 003 548 (dated May 18, 2010).
Japanese Patent Office, International Search Report in International Application No. PCT/JP2006/308711 (Aug. 8, 2006).

* cited by examiner

*Primary Examiner* — Frederick Krass
*Assistant Examiner* — Isaac Shomer
(74) *Attorney, Agent, or Firm* — Leydig, Voit & Mayer, Ltd.

(57) ABSTRACT

A granular preparation containing a biguanide compound and a solidification-preventive agent does not solidify during storage and can avoid the difficulty in dosing.

23 Claims, No Drawings

GRANULAR PREPARATION CONTAINING BIGUANIDE COMPOUND

TECHNICAL FIELD

The present invention relates to a stable granular preparation comprising a biguanide compound, which does not solidify during storage.

BACKGROUND ART

Biguanide compounds such as metformin and the like are effective for the treatment of non-insulin dependent diabetes mellitus and the like, and have been widely used for the superior efficacy thereof. As preparation, tablets are now in the market in Japan, Europe etc. and tablets and solutions are now in the market in the US.

In the biguanide compounds such as metformin and the like, tablets are bulky due to the high dose, which renders administration to the elderly, children and the like difficult. In diabetic patients, moreover, the dose often needs to be varied. However, control of the dose according to the symptom is difficult with tablets. While solutions are easy administration preparations which enable control of the dose, they are inferior to a solid preparation in the aspects of chemical stability, hygiene such as bacteriological control and the like. Granular preparations are easy to take, facilitate control of the dose, show good stability as compared to solutions because they are solids, and are associated with less hygiene problems.

As granular preparations of biguanide compounds such as metformin and the like, for example, patent reference 1 discloses preparations for oral administration (fine granules and granules) consisting of a biguanide compound and an organic acid.

As a method for preventing solidification of a granular or powder preparation, for example, patent reference 2 discloses a powder preparation for a restoration of compromised skin, which consists of sucrose, povidone-iodine, and a water-soluble carrier polymer selected from polyvinyl alcohol, polyvinylpyrrolidone, polyacrylic acid or a salt thereof, pullulan, carboxyvinyl polymer, methylcellulose, hydroxymethylcellulose, hydroxypropylmethylcellulose and carboxymethylcellulose or a salt thereof.

It is well known that selection of a solidification-preventive agent for a granular or powder preparation depends on the contained drug, and is an important issue. However, the above-mentioned references and the like do not at all disclose information relating to the solidification-preventive effect of the combination of a particular water-soluble carrier polymer or an inorganic compound and a particular drug, particularly a biguanide compound.

Pullulan is used as a base, a binder, a coating agent, a sugar coating agent or a diluent for use as a pharmaceutical additive, and used as a binder, a thickening agent, a moisturing agent, a film agent and the like for use as a food additive. Dextrin is used as an adsorbent, a binder, an adhesive, a thickening agent, a diluent, a dispersing agent and a disintegrant for use as a pharmaceutical additive. However, there is found no embodiment where pullulan or dextrin is used as a solidification-preventive agent of a granular preparation.

patent reference 1: JP-A-2002-512953
patent reference 2: JP-A-8-12582

DISCLOSURE OF THE INVENTION

Problems to be Solved by the Invention

The problem to be solved by the present invention is provision of a granular preparation comprising a biguanide compound such as metformin and the like, which does not solidify during storage.

Means of Solving the Problem

The present inventors have found a problem of a preparation for oral administration comprising a biguanide compound and an organic acid as disclosed in JP-A-2002-512953, in that the metformin granular preparation at a high content solidifies during storage depending on the property of the main drug and sometimes cannot be taken out from a container. In such case, oral administrability is considered to be impaired (difficulty in oral administration).

The present inventors have conducted intensive studies and found that by adding polyvinylpyrrolidone, methylcellulose, pullulan, sodium alginate, magnesium stearate, dextrin, calcium chloride, sodium polyacrylate or light anhydrous silicic acid to a granular preparation of a biguanide compound such as metformin and the like, the preparation is free of solidification during storage, and a stable preparation can be obtained, which resulted in the accomplishment of the present invention.

The present inventors have also found that when the solidification-preventive agent is pullulan or dextrin, palatability (taste and mouthfeel) is superior.

Accordingly, the present invention relates to

[1] a granular preparation comprising a biguanide compound and a solidification-preventive agent,

[2] the granular preparation according to [1], wherein the biguanide compound is metformin or a pharmaceutically acceptable salt thereof,

[3] the granular preparation according to [1], wherein the biguanide compound is metformin hydrochloride,

[4] the granular preparation according to any one of [1]-[3], wherein the solidification-preventive agent is polyvinylpyrrolidone, methylcellulose, pullulan, sodium alginate, magnesium stearate, dextrin, calcium chloride, sodium polyacrylate, light anhydrous silicic acid or a mixture thereof,

[5] the granular preparation according to any one of [1]-[3], wherein the solidification-preventive agent is pullulan or dextrin,

[6] the granular preparation according to any one of [1]-[3], wherein the solidification-preventive agent is pullulan,

[7] the granular preparation according to any one of [1]-[6], having a particle size of not more than 1700 μm,

[8] the granular preparation according to any one of [1]-[7], which is in a dosage form of an orally disintegrating form,

[9] the granular preparation according to any one of [1]-[8], further comprising a water-soluble sugar alcohol,

[10] the granular preparation according to [9], wherein the water-soluble sugar alcohol is erythritol,

[11] the granular preparation according to [10], wherein erythritol is contained in 10-90 wt % of the total,

[12] the granular preparation according to any one of [1]-[11], further comprising an organic acid,

[13] the granular preparation according to [12], wherein the organic acid is citric acid or malic acid,
[14] the granular preparation according to any one of [1]-[13], further comprising a high-intensity sweetener, or
[15] the granular preparation according to any one of [1]-[14], wherein the biguanide compound is contained in 10-90 wt % of the total, and the solidification-preventive agent is contained in 0.1-10 wt % of the total.

Effect of the Invention

According to the present invention, a granular preparation of a biguanide compound such as metformin and the like, which is free of solidification during storage, can be provided, whereby a preparation which is easy to take, facilitates control of the dose, shows good stability, and is associated with less hygiene problems can be provided.

BEST MODE FOR EMBODYING THE INVENTION

In the present invention, the biguanide compound represents drugs having a biguanide structure, and includes those in the form of a pharmaceutically acceptable salt such as hydrochloride and the like. Specific examples include metformin, buformin, phenformin or pharmaceutically acceptable salts thereof. Examples of preferable biguanide pharmaceutical agent include metformin and a pharmaceutically acceptable salt thereof, where metformin hydrochloride is more preferable.

The concentration of the biguanide compound such as metformin hydrochloride and the like in the present invention is not particularly limited. It is preferably 10-90% (wt %), more preferably 20-90% (wt %), more preferably 20-80% (wt %), particularly preferably 30-70% (wt %).

As the solidification-preventive agent in the present invention, for example, polyvinylpyrrolidone, methylcellulose, pullulan, sodium alginate, magnesium stearate, dextrin, calcium chloride, sodium polyacrylate or light anhydrous silicic acid and the like can be mentioned. Preferably, pullulan, dextrin, calcium chloride or light anhydrous silicic acid can be mentioned, more preferably, pullulan or dextrin can be mentioned, and particularly preferably, pullulan can be mentioned.

Pullulan in the present invention is generally a natural polysaccharide wherein maltotriose is regularly α-1,6 bonded, which is obtained from starch as a starting material by culturing Aureobasidium pullulans, which is one kind of Aureobasidium. Preferably, one free of modification such as introduction of substituent by chemical reaction and the like can be mentioned. Pullulan is not particularly limited as long as pharmaceutical use is acceptable, and preferably has an average molecular weight of 10-1000 thousand, more preferably 50-500 thousand, further preferably 100-300 thousand.

Dextrin in the present invention is a generic term of intermediate products up to maltose, which is generally obtained by a heat treatment of dry starch, and is a polysaccharide represented by the formula $(C_6H_{10}O_5)n.x H_2O$. Dextrin is not particularly limited as long as pharmaceutical use is acceptable, and preferably has an average molecular weight of 1000-20000, more preferably 2000-10000, further preferably 3000-6000.

The methods of adding a solidification-preventive agent in the present invention include, for example, a method including adding a solidification-preventive agent in the form of a powder to a granular preparation of a biguanide compound such as metformin and the like, a method including spraying a solution of a solidification-preventive agent on a granular preparation of a biguanide compound such as metformin and the like by a known production method, a method including spraying a solution of a solidification-preventive agent on a biguanide compound such as metformin and the like, granulating the compound to give a granular preparation, a method including mixing a biguanide compound such as metformin and the like and a solidification-preventive agent, and then producing a granular preparation by a known granulation method and the like.

As a preferable granular preparation, for example, a granular preparation containing a granular preparation of a biguanide compound such as metformin and the like and a solidification-preventive agent can be mentioned.

The method of obtaining the granular preparation of the present invention includes known granulation methods and, for example, extrusion-granulation method, fluidized bed granulation method, rotor granulation method and the like can be mentioned.

While the concentration of the solidification-preventive agent in the present invention is not particularly limited, it is generally 0.1-10% (wt %), preferably 0.5-9% (wt %), more preferably 1-8% (wt %), particularly preferably 2-7% (wt %).

The granular preparation in the present invention can also contain a nontoxic and inactive additive generally used in the field of preparations. Such additive includes one substantially free of an influence on the effect of the present invention, and generally used for oral preparation. Preferably, an additive used for an orally disintegrating dosage form that quickly dissolves in the oral cavity after administration is desirable. As such additive, for example, water-soluble sugar alcohol such as mannitol, erythritol, xylitol or sorbitol and the like can be mentioned. Particularly, use of erythritol preferably affords a preparation having better palatability (taste and mouthfeel).

In addition, a corrective such as organic acid (ascorbic acid, citric acid, malic acid, tartaric acid and the like) and the like, a high-intensity sweetener such as dipotassium glycyrrhizinate, saccharin, saccharin sodium, aspartame, acesulfame potassium, sucralose and the like, or an aromatizing agent a flavor (lemon, lemonlime, grape, plum, yogurt and the like) and the like can be added, in which case a more preferable palatability is obtained.

As preferable organic acid, citric acid or malic acid can be mentioned. As a representative organic acid, citric acid can be mentioned. As other representative organic acid, malic acid can be mentioned.

Erythritol in the present invention has a molecular weight of 122, which is obtained from glucose, obtained by enzyme hydrolysis of starch, as a starting material according to a fermentation method with a yeast. The concentration of erythritol is not particularly limited, and is preferably 10-90% (wt %), more preferably 10-80% (wt %), still more preferably 20-80% (wt %), particularly preferably 20-70% (wt %).

The granular preparation of the present invention is preferably formed as a granule having a particle size of not more than 1700 μm. When the particle size exceeds 1700 μm, a good palatability of a granular preparation is not often afforded. A preparation containing a granule having a particle size of not more than 850 μm and not less than 500 μm in not more than 5% of the total is called a powder and a preparation containing a granule of not more than 75 μm in not more than 10% is called a fine granule, which afford a more preferable palatability.

The dosage form of granular preparation also includes, for example, an orally disintegrating dosage form and the like. An orally disintegrating dosage form is characterized in that, for example, the total amount taken is dissolved or disintegrated to not more than 200 μm in the oral cavity within 30 seconds and the like. A fine granule or powder, whose total amount taken is dissolved or disintegrated to not more than 75 μm within 15 seconds, affords a more preferable palatability.

The orally disintegrating dosage form of the present invention has an average particle size of preferably 75-1700 μm, more preferably 75-850 μm, still more preferably 75-500 μm, particularly preferably 75-300 μm.

When an orally disintegrating dosage form contains pullulan and dextrin as solidification-preventive agents, the preparation is dissolved in the oral cavity particularly quickly, does not influence the taste, and makes palatability fine.

The present invention is explained in more detail in the following by referring to Examples, which are not to be construed as limitative.

EXAMPLE 1

The formulation and production methods of Examples 1-14 and Comparative Examples 1-16 are shown in the following.

TABLE 1

| composition | Ex. 1 | Ex. 2 | Ex. 3 | Ex. 4 | Ex. 5 | Ex. 6 | Ex. 7 |
|---|---|---|---|---|---|---|---|
| metformin hydrochloride | 1000 mg | 1000 mg | 1000 mg | 1000 mg | 1000 mg | 1000 mg | 1000 mg |
| erythritol | 3000 mg | 3000 mg | 3000 mg | 3000 mg | 3000 mg | 3000 mg | 3000 mg |
| sucralose | 100 mg | 100 mg | 100 mg | 100 mg | 100 mg | 100 mg | 100 mg |
| citric acid | 40 mg | 40 mg | 40 mg | 40 mg | 40 mg | 40 mg | 40 mg |
| corn starch | 25 mg | 25 mg | 25 mg | 25 mg | 25 mg | 25 mg | 25 mg |
| polyvinylpyrrolidone | 219 mg | — | — | — | — | — | — |
| methylcellulose | — | 219 mg | — | — | — | — | — |
| pullulan | — | — | 219 mg | — | — | — | — |
| dextrin | — | — | — | 219 mg | — | — | — |
| sodium alginate | — | — | — | — | 219 mg | — | — |
| calcium chloride | — | — | — | — | — | 219 mg | — |
| magnesium stearate | — | — | — | — | — | — | 219 mg |

TABLE 2

| composition | Ex. 8 | Ex. 9 | Ex. 10 | Ex. 11 |
|---|---|---|---|---|
| metformin hydrochloride | 1000 mg | 1000 mg | 1000 mg | 1000 mg |
| erythritol | 3000 mg | 3000 mg | 1700 mg | 800 mg |
| sucralose | 100 mg | 100 mg | 70 mg | 15 mg |
| citric acid | 40 mg | 40 mg | 30 mg | 50 mg |
| corn starch | 25 mg | 25 mg | 9.3 mg | 10 mg |
| sodium polyacrylate | 219 mg | — | — | — |
| light anhydrous silicic acid | — | 85 mg | — | — |
| pullulan | — | — | 148 mg | 99 mg |

TABLE 3

| composition | Ex. 12 | Ex. 13 | Ex. 14 |
|---|---|---|---|
| metformin hydrochloride | 1000 mg | 1000 mg | 1000 mg |
| erythritol | 1750 mg | 1750 mg | 1750 mg |
| sucralose | 30 mg | 30 mg | 30 mg |
| malic acid | 40 mg | 40 mg | 40 mg |
| corn starch | 15 mg | 15 mg | 15 mg |
| calcium chloride | 149 mg | — | — |
| dextrin | — | 149 mg | — |
| pullulan | — | — | 149 mg |

TABLE 4

| composition | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|
| metformin hydrochloride | 1000 mg | 1000 mg | 1000 mg | 1000 mg | 1000 mg | 1000 mg | 1000 mg |
| erythritol | 3000 mg | 3000 mg | 3000 mg | 3000 mg | 3000 mg | 3000 mg | 3000 mg |
| sucralose | 100 mg | 100 mg | 100 mg | 100 mg | 100 mg | 100 mg | 100 mg |
| citric acid | 40 mg | 40 mg | 40 mg | 40 mg | 40 mg | 40 mg | 40 mg |
| corn starch | 25 mg | 25 mg | 25 mg | 25 mg | 25 mg | 25 mg | 25 mg |
| polyvinyl alcohol | 219 mg | — | — | — | — | — | — |
| carboxyvinyl polymer | — | 219 mg | — | — | — | — | — |

TABLE 4-continued

| composition | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|
| hydroxypropyl cellulose | — | — | 219 mg | — | — | — | — |
| hydroxypropyl methylcellulose | — | — | — | 219 mg | — | — | — |
| lactose | — | — | — | — | 219 mg | — | — |
| calcium carbonate | — | — | — | — | — | 219 mg | — |
| anhydrous dibasic calcium phosphate | — | — | — | — | — | — | 219 mg |

TABLE 5

| composition | Com. Ex. 8 | Com. Ex. 9 | Com. Ex. 10 | Com. Ex. 11 | Com. Ex. 12 | Com. Ex. 13 | Com. Ex. 14 |
|---|---|---|---|---|---|---|---|
| metformin hydrochloride | 1000 mg | 1000 mg | 1000 mg | 1000 mg | 1000 mg | 1000 mg | 1000 mg |
| erythritol | 3000 mg | 3000 mg | 3000 mg | 3000 mg | 3000 mg | 3000 mg | 1700 mg |
| sucralose | 100 mg | 100 mg | 100 mg | 100 mg | 100 mg | 100 mg | 70 mg |
| citric acid | 40 mg | 40 mg | 40 mg | 40 mg | 40 mg | 40 mg | 30 mg |
| corn starch | 25 mg | 25 mg | 25 mg | 25 mg | 25 mg | 25 mg | 9.3 mg |
| calcium stearate | 219 mg | — | — | — | — | — | — |
| polyacrylic acid | — | 219 mg | — | — | — | — | — |
| carboxymethyl-cellulose | — | — | 219 mg | — | — | — | — |
| carboxymethyl-cellulose sodium | — | — | — | 219 mg | — | — | — |
| carboxymethyl-cellulose calcium | — | — | — | — | 219 mg | — | — |

TABLE 6

| composition | Com. Ex. 15 | Com. Ex. 16 |
|---|---|---|
| metformin hydrochloride | 1000 mg | 1000 mg |
| erythritol | 800 mg | 1750 mg |
| sucralose | 15 mg | 30 mg |
| citric acid | 50 mg | — |
| malic acid | — | 40 mg |
| corn starch | 10 mg | 15 mg |

EXAMPLES 1-8

Metformin hydrochloride (200 g), citric acid (8 g), sucralose (20 g) and erythritol (600 g) were mixed. Corn starch (5 g) was dissolved in purified water (495 g), heated to 95° C., cooled to ambient temperature and purified water was added to the total weight of 500 g to give a binding solution. Using the binding solution, the mixture was granulated in a fluidized bed granulator, and dried to give metformin hydrochloride orally disintegrating fine granules. The fine granules (95 g) were mixed with polyvinylpyrrolidone, methylcellulose, pullulan, dextrin, sodium alginate, calcium chloride, magnesium stearate or sodium polyacrylate (each 5 g).

EXAMPLE 9

In the same manner as in Examples 1-8, metformin hydrochloride orally disintegrating fine granules were prepared. The fine granules (98 g) were mixed with light anhydrous silicic acid (2 g).

EXAMPLE 10

Metformin hydrochloride (300 g), citric acid (9 g), sucralose (21 g) and erythritol (510 g) were mixed. Corn starch (2.8 g) was dissolved in purified water (277.2 g), heated to 95° C., cooled to ambient temperature and purified water was added to the total weight of 280 g to give a binding solution. Using the binding solution, the mixture was granulated in a fluidized bed granulator, and dried to give metformin hydrochloride orally disintegrating fine granules. The fine granules (95 g) were mixed with pullulan (5 g).

EXAMPLE 11

Metformin hydrochloride (700 g), citric acid (35 g), sucralose (10.5 g) and erythritol (560 g) were mixed. Corn starch (7 g) was dissolved in purified water (630 g), heated to 95° C., cooled to ambient temperature and purified water was added to the total weight of 700 g to give a binding solution. Using the binding solution, the mixture was granulated in a fluidized bed granulator, and dried to give metformin hydrochloride fine granules. The fine granules (95 g) were mixed with pullulan (5 g).

EXAMPLES 12-14

Metformin hydrochloride (460 g), malic acid (18.4 g), sucralose (13.8 g) and erythritol (805 g) were mixed. Corn starch (7 g) was dissolved in purified water (630 g), heated to 95° C., cooled to ambient temperature and purified water was added to the total weight of 700 g to give a binding solution. Using the binding solution, the mixture was granulated in a fluidized bed granulator, and dried to give metformin hydrochloride orally disintegrating fine granules. The fine granules (95 g) were mixed with calcium chloride and pullulan or dextrin (each 5 g).

COMPARATIVE EXAMPLES 1-12

In the same manner as in Examples 1-8, metformin hydrochloride orally disintegrating fine granules were prepared.

The fine granules (95 g) were mixed with polyvinyl alcohol, carboxyvinyl polymer, hydroxypropylcellulose, hydroxypropylmethylcellulose, lactose, calcium carbonate, anhydrous dibasic calcium phosphate, calcium stearate, polyacrylic acid, carboxymethylcellulose, carboxymethylcellulose sodium or carboxymethylcellulose calcium (each 5 g).

COMPARATIVE EXAMPLE 13

In the same manner as in Examples 1-8, metformin hydrochloride orally disintegrating fine granules were prepared.

COMPARATIVE EXAMPLE 14

In the same manner as in Example 10, metformin hydrochloride orally disintegrating fine granules were prepared.

COMPARATIVE EXAMPLE 15

In the same manner as in Example 11, metformin hydrochloride fine granules were prepared.

COMPARATIVE EXAMPLE 16

In the same manner as in Examples 12-14, metformin hydrochloride orally disintegrating fine granules were prepared.

EXPERIMENTAL EXAMPLE 1

Stability

Using fine granules obtained in Examples 1-14 and Comparative Examples 1-16, a stability testing was performed. Fine granules (5 g) were each placed in glass containers, which were tightly sealed and stored at 40° C. for 1 week.

Appearance of metformin hydrochloride fine granules after storage at 40° C. for 1 week

TABLE 7

| samples | organic acid | additive | results |
| --- | --- | --- | --- |
| Ex. 1 | citric acid | polyvinylpyrrolidone | o |
| Ex. 2 | | methylcellulose | o |
| Ex. 3 | | pullulan | o |
| Ex. 4 | | dextrin | o |
| Ex. 5 | | sodium alginate | o |
| Ex. 6 | | calcium chloride | o |
| Ex. 7 | | magnesium stearate | o |
| Ex. 8 | | sodium polyacrylate | o |
| Ex. 9 | | light anhydrous silicic acid | o |
| Ex. 10 | | pullulan | o |
| Ex. 11 | | pullulan | o |
| Ex. 12 | malic acid | calcium chloride | o |
| Ex. 13 | | dextrin | o |
| Ex. 14 | | pullulan | o |
| Com. Ex. 1 | citric acid | polyvinyl alcohol | x |
| Com. Ex. 2 | | carboxyvinyl polymer | x |
| Com. Ex. 3 | | hydroxypropylcellulose | x |
| Com. Ex. 4 | | hydroxypropylmethylcellulose | x |
| Com. Ex. 5 | | lactose | x |
| Com. Ex. 6 | | calcium carbonate | x |
| Com. Ex. 7 | | anhydrous dibasic calcium phosphate | x |
| Com. Ex. 8 | | calcium stearate | x |
| Com. Ex. 9 | | polyacrylic acid | x |
| Com. Ex. 10 | | carboxymethylcellulose | x |
| Com. Ex. 11 | | carboxymethylcellulose sodium | x |
| Com. Ex. 12 | | carboxymethylcellulose calcium | x |
| Com. Ex. 13 | | free | x |
| Com. Ex. 14 | | free | x |
| Com. Ex. 15 | | free | x |
| Com. Ex. 16 | malic acid | free | x |

Appearance
o: the contents flow when small portion container is turned around 180 degrees, or slight physical stimulation restores flowability.
x: the contents do not flow at all when small container is turned around 180 degrees, or mass is present which is not disintegrated upon physical stimulation.

When polyvinylpyrrolidone, methylcellulose, pullulan, sodium alginate, dextrin, magnesium stearate, calcium chloride, sodium polyacrylate or light anhydrous silicic acid was added to the fine granules, a solidification-preventive effect was observed at 40° C. Polyvinyl alcohol, carboxyvinyl polymer, hydroxypropylcellulose, hydroxypropylmethylcellulose, lactose, calcium carbonate, anhydrous dibasic calcium phosphate, calcium stearate, polyacrylic acid, carboxymethylcellulose, carboxymethylcellulose sodium and carboxymethylcellulose calcium did not show a solidification-preventive effect.

EXPERIMENTAL EXAMPLE 2

Palatability

EXAMPLES 15-16

In the same manner as in Examples 1-8, metformin hydrochloride orally disintegrating fine granules were prepared. The fine granules (95 g) were mixed with a flavor (Yogurt Micron H-85180, manufactured by Takasago International Corporation) (0.1 g) and pullulan or dextrin (5 g).

EXAMPLE 17

In the same manner as in Example 10, metformin hydrochloride orally disintegrating fine granules were prepared. The fine granules (95 g) were mixed with a flavor (Lemon Micron H-80661, manufactured by Takasago International Corporation) (0.1 g) and pullulan (5 g).

EXAMPLES 18-19

In the same manner as in Examples 12-14, metformin hydrochloride orally disintegrating fine granules were prepared. The fine granules (95 g) were mixed with a flavor (Lemon Micron H-80661, manufactured by Takasago International Corporation) (0.1 g) and pullulan or dextrin (5 g).

COMPARATIVE EXAMPLES 17-21

In the same manner as in Examples 1-8, metformin hydrochloride orally disintegrating fine granules were prepared. The fine granules (95 g) were mixed with a flavor (Yogurt Micron H-85180, manufactured by Takasago International Corporation) (0.1 g) and polyvinylpyrrolidone, methylcellulose, sodium alginate, calcium chloride or magnesium stearate (5 g).

COMPARATIVE EXAMPLE 22

In the same manner as in Examples 1-8, metformin hydrochloride orally disintegrating fine granules were prepared. The fine granules (98 g) were mixed with a flavor (Yogurt Micron H-85180, manufactured by Takasago International Corporation) (0.1 g) and light anhydrous silicic acid (2 g).

COMPARATIVE EXAMPLE 23

In the same manner as in Examples 12-14, metformin hydrochloride orally disintegrating fine granules were prepared. The fine granules (95 g) were mixed with a flavor (Lemon Micron H-80661, manufactured by Takasago International Corporation) (0.1 g) and calcium chloride (5 g).

The orally disintegrating fine granules (1 g) obtained in Examples 15-19 and Comparative Examples 17-23 were placed in the mouth, and the dissolution time thereof was measured. In addition, they were compared with a control fine granules free of the solidification-preventive agent in the taste and palatability (taste and mouthfeel, particularly when dissolving). After the completion of the test, fine granules were spit out and the oral cavity was thoroughly rinsed with water. Dissolution Time, Taste and Palatability

TABLE 8

| samples | additives | organic acid | dissolution time | palatability |
|---|---|---|---|---|
| Ex. 15 | pullulan | citric acid | 5-10 sec | good |
| Ex. 16 | dextrin | | 5-10 sec | good |
| Ex. 17 | pullulan | | 5-10 sec | good |
| Ex. 18 | dextrin | malic acid | 5-10 sec | good |
| Ex. 19 | pullulan | | 5-10 sec | good |
| Com. Ex. 17 | polyvinylpyrrolidone | citric acid | 5-10 sec | baddish |
| Com. Ex. 18 | methylcellulose | | 5-10 sec | bad |
| Com. Ex. 19 | sodium alginate | | 5-10 sec | bad |
| Com. Ex. 20 | calcium chloride | | 5-10 sec | bad |
| Com. Ex. 21 | magnesium stearate | | 5-10 sec | bad |
| Com. Ex. 22 | light anhydrous silicic acid | | 5-10 sec | bad |
| Com. Ex. 23 | calcium chloride | malic acid | 5-10 sec | bad |
| control | free | citric acid | 5-10 sec | good |
| | | malic acid | 5-10 sec | good |

The fine granules of Examples 15-19 were quickly dissolved in 5-10 seconds in the oral cavity, the solidification-preventive agent did not affect the taste, and palatability was good. While the dissolution property was good in Comparative Examples 17-23, the solidification-preventive agent influenced palatability (taste and mouthfeel).

From the aspect of palatability, it is understood that pullulan and dextrin are particularly superior as solidification-preventive agents for orally disintegrating fine granules.

Industrial Applicability

The present invention enables provision of a stable granular preparation of a biguanide compound such as metformin hydrochloride granular preparation and the like, which is free from solidification during storage. In addition, the present invention enables provision of a preparation which is easy to take, facilitates control of the dose, shows good stability, and is associated with less hygiene problems.

The invention claimed is:

1. A granular preparation comprising (a) metformin or a pharmaceutically acceptable salt thereof, (b) an organic acid in an amount effective to increase palatability, said acid being selected from the group consisting of citric acid and malic acid, and (c) a solidification-preventive agent selected from the group consisting of pullulan, dextrin, calcium chloride, light anhydrous silicic acid, and mixtures thereof,
wherein
the metformin or pharmaceutically acceptable salt thereof is present in an amount of 10-90 wt % of the total,
and the solidification-preventive agent is present in an amount of 0.5-10 wt % of the total.

2. The granular preparation according to claim 1, wherein (a) is metformin hydrochloride.

3. The granular preparation according to claim 1, wherein the solidification-preventive agent is dextrin.

4. The granular preparation according to claim 1, wherein the solidification-preventive agent is pullulan.

5. The granular preparation according to claim 1, having a particle size of not more than 1700 μm.

6. The granular preparation according to claim 1, which is in a dosage form of an orally disintegrating form.

7. The granular preparation according to claim 1, further comprising a water-soluble sugar alcohol.

8. The granular preparation according to claim 7, wherein the water-soluble sugar alcohol is erythritol.

9. The granular preparation according to claim 8, wherein erythritol is contained in 10-90 wt % of the total.

10. The granular preparation according to claim 1, further comprising a high-intensity sweetener.

11. The granular preparation according to claim 7, further comprising a high-intensity sweetener.

12. The granular preparation according to claim 7, wherein the solidification-preventive agent is dextrin.

13. The granular preparation according to claim 2, wherein the solidification-preventive agent is dextrin.

14. The granular preparation according to claim 7, wherein the solidification-preventive agent is pullulan.

15. The granular preparation according to claim 2, wherein the solidification-preventive agent is pullulan.

16. The granular preparation according to claim 1, wherein the organic acid is citric acid.

17. The granular preparation according to claim 1, wherein the solidification-preventive agent is present in an amount of 1-10 wt % of the total.

18. The granular preparation according to claim 1, wherein the solidification-preventive agent is present in an amount of 2-10 wt % of the total.

19. The granular preparation according to claim 4, wherein the organic acid is citric acid.

20. The granular preparation according to claim 4, wherein the solidification-preventive agent is present in an amount of 1-10 wt % of the total.

21. The granular preparation according to claim 4, wherein the solidification-preventive agent is present in an amount of 2-10 wt % of the total.

22. The granular preparation according to claim 1, wherein citric acid is present in an amount of 0.9 wt % of the total.

23. The granular preparation according to claim 1, wherein malic acid is present in an amount of 1.3 wt % of the total.

* * * * *